United States Patent [19]

Vacanti et al.

[11] Patent Number: 5,567,612
[45] Date of Patent: Oct. 22, 1996

[54] GENITOURINARY CELL-MATRIX STRUCTURE FOR IMPLANTATION INTO A HUMAN AND A METHOD OF MAKING

[75] Inventors: Joseph P. Vacanti, Winchester; Michael R. Freeman, Boston, both of Mass.

[73] Assignees: Massachusetts Institute of Technology, Cambridge; Children's Medical Center Corporation, Boston, both of Mass.

[21] Appl. No.: 98,569

[22] Filed: Jul. 27, 1993

Related U.S. Application Data

[63] Continuation of Ser. No. 781,898, Oct. 24, 1991, abandoned, which is a continuation-in-part of Ser. No. 679,177, Mar. 26, 1991, abandoned, which is a continuation of Ser. No. 401,648, Aug. 30, 1989, abandoned, which is a continuation of Ser. No. 123,579, Nov. 20, 1987, abandoned, which is a continuation-in-part of Ser. No. 933,018, Nov. 20, 1986, abandoned.

[51] Int. Cl.$^6$ .............................. C12N 5/00; A01N 1/02; A01N 63/00; A61F 2/02; A61F 2/04; A61F 13/00; A61F 2/00; A61K 9/14

[52] U.S. Cl. .................... 435/240.23; 435/240.1; 435/240.2; 435/240.243; 435/1; 623/11; 623/12; 424/93.7; 424/422; 424/423; 424/426; 424/486

[58] Field of Search ............................ 435/240.1, 240.23, 435/240.243, 240.242, 180, 240.2, 1; 424/422, 423, 426, 486; 436/823; 524/24; 525/421; 623/11, 12, 13

[56] References Cited

U.S. PATENT DOCUMENTS

| | | | |
|---|---|---|---|
| 2,609,347 | 9/1952 | Wilson | 260/2.5 |
| 2,653,917 | 9/1953 | Hammon | 260/25 |
| 2,659,935 | 11/1953 | Hammon | 18/55 |
| 2,664,367 | 12/1953 | Wilson | 117/138.8 |
| 2,846,407 | 8/1958 | Wilson | 260/2.5 |
| 3,826,241 | 7/1974 | Bucalo | 128/1 |
| 3,880,991 | 4/1975 | Yollesa | 424/22 |
| 3,883,393 | 5/1975 | Knazek et al. | 195/1.8 |
| 3,902,497 | 9/1975 | Casey | 128/296 |
| 3,949,073 | 4/1976 | Daniels | 424/177 |
| 3,960,150 | 6/1976 | Hussain et al. | 128/260 |
| 3,974,526 | 8/1976 | Dardik et al. | 3/1.4 |
| 3,992,725 | 11/1976 | Homsy | 3/1 |
| 4,026,304 | 5/1977 | Levy | 128/419 |
| 4,069,307 | 1/1978 | Higuchi et al. | 424/22 |
| 4,137,921 | 2/1979 | Okuzumi | 128/335.5 |
| 4,141,087 | 2/1979 | Shalaby et al. | 3/1 |
| 4,186,448 | 2/1980 | Brekke | 3/1.9 |
| 4,192,827 | 3/1980 | Mueller et al. | 525/123 |
| 4,205,399 | 6/1980 | Shalaby et al. | 3/1 |
| 4,239,664 | 12/1980 | Teng et al. | 260/17.9 |
| 4,243,775 | 1/1981 | Rosensaft et al. | 525/415 |
| 4,277,582 | 7/1981 | Mueller et al. | 525/421 |
| 4,280,954 | 7/1981 | Yannas et al. | 260/123.7 |
| 4,304,591 | 12/1981 | Mueller et al. | 71/93 |
| 4,304,866 | 12/1981 | Green et al. | 435/240 |
| 4,347,847 | 9/1982 | Usher | 128/334 |
| 4,348,329 | 9/1982 | Chapman | 260/403 |
| 4,352,883 | 10/1982 | Lim | 435/178 |
| 4,391,797 | 7/1983 | Folkman et al. | 424/19 |
| 4,416,986 | 11/1983 | Markus et al. | 435/68 |
| 4,431,428 | 2/1984 | Schmer | 604/897 |
| 4,438,198 | 3/1984 | Schmer | 435/178 |
| 4,439,152 | 3/1984 | Small | 433/173 |
| 4,440,921 | 4/1984 | Allcock et al. | 528/168 |
| 4,446,234 | 5/1984 | Russo et al. | 435/29 |
| 4,450,150 | 5/1984 | Sidman | 424/1.1 |
| 4,456,687 | 6/1984 | Green | 435/241 |
| 4,485,096 | 11/1984 | Bell | 424/95 |
| 4,495,174 | 1/1985 | Allcock et al. | 424/78 |
| 4,505,266 | 3/1985 | Yannas et al. | 128/1 |
| 4,520,821 | 6/1985 | Schmidt et al. | 128/334 |
| 4,544,516 | 10/1985 | Hughes et al. | 264/108 |
| 4,545,082 | 10/1985 | Hood | 623/1 |
| 4,546,500 | 10/1985 | Bell | 623/1 |
| 4,563,490 | 1/1986 | Stöl et al. | 524/24 |
| 4,576,608 | 3/1986 | Homsy | 623/11 |
| 4,637,931 | 1/1987 | Schmitz | 424/78 |
| 4,675,189 | 6/1987 | Kent et al. | 424/490 |
| 4,681,763 | 7/1987 | Nathanson et al. | 424/98 |
| 4,721,096 | 1/1988 | Naughton et al. | 128/1 |

(List continued on next page.)

FOREIGN PATENT DOCUMENTS

| | | |
|---|---|---|
| 0282746 | 9/1988 | European Pat. Off. . |
| 0339607 | 11/1989 | European Pat. Off. . |
| WO87/06120 | 4/1987 | WIPO . |
| WO89/00413 | 7/1988 | WIPO . |

OTHER PUBLICATIONS

Vacanti, et al J Pediatric Surgery 23(1) 3–9 1988.
Thuroff, et al Urology 21(2) 155–158 1983.
Freshney, *Animal Cell Culture, a practical Approach* IRL Press, 1986.

(List continued on next page.)

*Primary Examiner*—Michael G. Wityshyn
*Assistant Examiner*—Susan M. Dadio
*Attorney, Agent, or Firm*—Arnall Golden & Gregory

[57] ABSTRACT

Methods and artificial matrices for the growth and implantation of urological structures and surfaces are disclosed in which urothelial cells are grown in culture on biodegradable, biocompatible, fibrous matrices formed of polymers, such as polyglycolic acid, polylactic acid, or other polymers which degrade over time. The cells can be cultured in vitro until an adequate cell volume and density has developed for the cells to survive and proliferate in vivo. Alternatively, when adequate cell numbers for implantation are available, the cells can be attached to the matrix and implanted directly, without proliferation in vitro. The implants approximate the desired urological structure to be replaced or repaired, such as the kidney, urether, bladder, urethra, and the like. Implantation is followed by remodeling through cell growth and proliferation in vivo. In another aspect of the invention, techniques are disclosed for selectively extracting or harvesting urothelial cells either from excised urological tissue in vitro or from intact urological tissue in vivo by treating the tissue with a digestive enzyme, such as collagenase.

11 Claims, No Drawings

U.S. PATENT DOCUMENTS

| | | | |
|---|---|---|---|
| 4,757,128 | 7/1988 | Domb | 528/271 |
| 4,853,324 | 8/1989 | Viles | 435/2 |
| 4,868,121 | 9/1989 | Scharp et al. | 435/268 |
| 4,880,622 | 11/1989 | Allcock et al. | 424/78 |
| 4,891,225 | 1/1990 | Langer et al. | 424/428 |
| 4,946,938 | 8/1990 | Magill | 528/399 |
| 4,963,489 | 10/1990 | Naughton et al. | 435/240.1 |
| 4,988,761 | 1/1991 | Ikada et al. | 524/557 |
| 5,032,508 | 7/1991 | Naughton et al. | 435/32 |

OTHER PUBLICATIONS

Alberts, et al., *Molecular Biology of the Cell*, 893 and 894 (1983).

Allcock, et al., *Macromolecule* 10:824–830 (1977).

Allcock, H. R., et al., *Inorg. Chem.* 11,2584 (1972).

Allcock, et al., *Macromolecules* 16, 715 (1983).

Allcock, et al., *Macromolecules* 19, 1508 (1986).

Allcock, et al., *Biomaterials*, 9, 500 (1988).

Allcock, et al., *Macromolecules* 21, 1980 (1988).

Allcock, et al., *Inorg. Chem.* 21(2), 515–521 (1982).

Allcock, et al., *Macromolecules* 22, 75 (1989).

Anderson, David J. et al., *Caltech Biology* (1987), p. 177.

Anderson, Kathryn D., et al., "Gene Expression in Impanted Rat Hepatocytes Following Retroviral–Mediated Gene Transfer," *Somatic Cell and Molecular Genetics*, vol. 15, pp. 215–227 (1989).

Backlund, Erik–Olof, et al., "Toward a Transplantation Therapy in Parkinson's Disease," *Annals of the N.Y. Academy of Science*, vol. 495, pp. 658–673 (1987).

Ben–Ze'ev, A., et al., "Cell–Cell and Cell–Matrix Interactions Differentially Regulate the Expression of Hepatic and Cytoskeletal Genes in Primary Cultures of Rat Hepatocytes," *Proc. Natl. Acad. Sci, USA* vol. 85, pp. 2161–2165 (Apr. 1988).

Berrino, Pietro, et al., "Surgical Correction of Breast Deformities Following Long–Lasting Complications of Polyurethane–Covered Implants," *Ann. Plast. Surg.*, 24:481 (1990).

Biers, Elizabeth, "Organogensis' Human Artery Equivalent May Revolutionize Vascular Grafts," *Genetic Engineering News*, (Nov.–Dec. 1987).

Bissell, D. Montgomery, et al., "Interactions of Rat Hepatocytes with Type IV Collagen, Fibronectin and Laminin Matrices, Distinct Matrix–Controlled Modes of Attachment and Spreading," *European Journal of Cell Biology* 40, 72–78 (1986).

Bissell, D. M., et al., "Support of Cultured Hepatocytes by a Laminin–Rich Gel, Evidence of a Functionally Significant Subendothelial Matrix in Normal Rat Liver," *J. Clin. Invest.*, vol. 79, pp. 801–812 (Mar. 1987).

Bissell, D. M., et al., "The Role of Extracellular Matrix in Normal Liver," *Scand. J. Gastroenterol.* 23:107 (1988).

Björklund, A., *Annals of the N.Y. Academy of Science*, vol. 495, pp. 676–686 (1987).

Bohn, M. C., et al., "Adrenal Medulla Grafts Enhance Recovery of Striatal Dopaminergic Fibers," *Science* 238(4817):913–6 (Aug. 21, 1987).

"Brain Graft Seeks to Relieve Huntington Disease Patient," *The New York Times*, (Mar. 4, 1988).

Children's Hospital (The), Department of Nursing Division 5, "Liver Transplantation," (May 1984).

Chuang, Vincent P., et al., "Sheath Needle for Liver Biopsy in High–Risk Patients," *RSNA* pp. 261–262 (1988).

Collier, T. J., et al., "Norepinephrine Deficiency and Behavioral Senescence in Aged Rats: Transplanted Locus Ceruleus Neurons as an Experimental Replacement Therapy," *Annals of the New York Academy of Sciences* vol. 495:396–403 (New York 1987).

Craig, et al., "A Biologic Comparison of Polyglactin 910 and Polyglycolic Acid Synthetic Absorbable Sutures," *Surgery Gynecology & Obstetrics*, vol. 141, No. 1, pp. 1–10 (Jul. 1975).

Culliton, Barbara J., "Gore Tex Organoids and Genetic Drugs," *Science*, vol. 246, pp. 747–749 (Nov. 1989).

Davis, George E., et al., "Human Amnion Membrane Serves as a Substratum for Growing Axons In Vitro and Vivo," *Science*, vol. 236, pp. 1106–1109 (May 29, 1987).

da Silva, C. F., et al., "An In Vivo Model to Quantify Motor and Sensory Peripheral Nerve Regeneration Using Bioresorbable Nerve Guide Tubes," *Brain Research*, vol. 342, pp. 307–315 (1985).

del Cerro, M., et al., "Retinal Transplants into the Anterior Chamber of the Rat Eve," *Neuroscience* vol. 21(3):707–23 (Jun. 1987).

Doillon, C. J., et al., "Collagen–Based Wound Dressings: Control of the Pore Structure and Morphology," *Journal of Biomedical Materials Research*, vol. 20, pp. 1219–1228 (1986).

Doillon, C. J. et al., "Epidermal Cells Cultured on a Collagen–Based Material," G. W. Bailey, Editor, *Proceedings of the 44th Annual Meeting of the Electron Microscopy Society of America*, (1986). pp. 212–213.

Folkman, Judah, et al., "Angiogenic Factors," *Science*, vol. 235, pp. 442–447 (Jan. 23, 1987).

Gash, D. M., et al., "Amitotic Neuroblastoma Cells Used for Neural Implants in Monkeys," *Science*, 233(4771):1420–2 (Sep. 26, 1986).

Gash, D. M., "Neural Transplantation: Potential Therapy for Alzheimer's Disease," *J. Neural Transm.* [Suppl.] 24:301–8 (1987).

Grande, Daniel A., et al., "Healing of Experimentally Produced Lesions in Articular Cartilage Following Chondrocyte Transplantation," *The Anatomical Record* 218:142–148 (1987).

Grande, Daniel A., et al., "The Repair of Experimentally Produced Defects in Rabbit Articular Cartilage by Autologous Chondrocyte Transplantation," (May 11, 1988). manuscript.

Harris, A. K., et al., "Silicone Rubber Substrate: A New Wrinkle in the Study of Cell Locomotion," *Science (Wash. D.C.)* 208:177–179 (1980).

Henry, E. W., et al. "Nerve Regeneration Through Biodegradable Polyester Tubes," *Exp. Neurol.*, 90(3):652–76 (Dec. 1985).

Ingber, D. E., et al., "Cells as Tensegrity Structures: Architectural Regulation of Histodifferentiation by Physical Forces Transduced Over Basement Membrane," *Gene Expression During Normal and Malignant Differentiation*, L. C. Andersson, et al., editors, pp. 13–32 (Academic Press, Orlando, FL 1985).

Ingber, et al., "Endothelial Growth Factors and Extracellular Matrix Regulate DNA Synthesis Through Modulation of Cell and Nuclear Expansion," *In Vitro Cellular & Developmental Biology*, vol. 23, No. 5 pp. 387–394 (May 1987).

Ingber, et al., "Control of Capillary Morphogenesis: A Molecular System of Mechanical Switches," *J. Cell Biol.*, 107:797a (1988). Abstract.

Ingber, et al., "Growth Control through Fibronectin–Dependent Modulation of Cell Shape", *J. Cell Biol.*, 105:219a (1987). Abstract.

Ingber, et al., "How Does Extracellular Matrix Control Capillary Morphogenesis?", *Cell*, vol. 58, pp. 803–805 (Sep. 8, 1989).

Ingber, et al., "Mechanochemical Switching Between Growth and Differentiation During Fibroblast Growth Factor–Stimulated Angiogenesis Vitro: Role of Extracellular Matrix," *J. Cell Biol.*, vol. 109, pp. 317–330 (1989).

Jauregui, H. O., et al., "Attachment and Long Term Survival of Adult Rat Hepatocytes in Primary Monolayer Cultures: Comparison of Different Substrata and Tissue Culture Media Formulations," *In Vitro Cellular & Development Biology*, vol. 22, No. 1, pp. 13–22 (Jan. 1986).

Kleinman, H. K., et al. "Use of Extracellular Matrix Components for Cell Culture," *Analytical Biochemistry* 166, 1–13 (1987).

Kolata, Gina, "Parkinson Procedure: Fervor Turns to Disillusion," *The New York Times*, (Apr. 21, 1988).

Kordower, J. H., et al., "An in Vivo and in Vitro Assessment of Differentiated Neuroblastoma Cells as a Source of Donor Tissue for Transplantation," *Annals of the New York Academy of Scineces*, vol. 495, pp. 606–622 (New York 1987).

Kordower, J. H., et al., "Neuroblastoma Cells in Neural Transplants: A Neuroanatomical and Behavioral Analysis," *Brain Research*, 417(1):85–98 (Aug. 4, 1987).

Leong, K. W., et al., "Bioerodible Polyanhydrides as Drug–Carriers Matrices, I: Characterization, Degradation, and Release Characteristics," *Journal of Biomedical Materials Research*, vol. 19, 941–955 (1985).

Letourneau, "Possible Roles for Cell–to–Substratum Adhesion in Neuronal Morphogenesis," *Developmental Biology*, 44, 77–91 (1975).

Lewin, "Cloud over Parkinson's Therapy," *Science*, vol. 240, pp. 390–392, (Apr. 22, 1988).

Lewin, "Disappointing Brain Graft Results," *Science*, p. 1407, (Jun. 10, 1988).

Li, M. L., et al., "Influence of a Reconstituted Basement Membrane and Its Components on Casein Gene Expression and Secretion in Mouse Mammary Epithelial Cells," *Proc. Natl. Acad. Sci. USA* vol. 84, pp. 136–140 (Jan. 1987).

Macklis, J. D., et al., "Cross–Linked Collagen Surface for Cell Culture that is Stable, Uniform, and Optically Superior to Conventional Surfaces," *In Vitro Cellular & Developmental Biology*, vol. 21, No. 3, part I, pp. 189–194 (Mar. 1985).

Madison, R., et al, "Increased Rate of Peripheral Nerve Regeneration Using Bioresorbable Nerve Guides and a Laminin–Containing Gel," *Exp. Neurol.*, 88(3):767–72 (Jun. 1985).

Madison, R., et al., "Nontoxic Nerve Guide Tubes Support Neovascular Growth in Transected Rat Optic Nerve," *Exp Neurol*, 86(3):448–61 (Dec. 1984).

Madison, R., et al., "Peripheral Nerve Regeneration With Entubulation Repair: Comparison of Biodegradable Nerve Guides Versus Polyethylene Tubes and the Effects of a Laminin–Containing Gel," *Exp Neurol*, 95(2):387–90 (Feb. 1987).

Marciano, F. F., et al., "Structural and Functional Relationships of Grafted Vasopressin Neurons," *Brain Res.*, 370(2):338–42 (Apr. 9, 1986).

Mesnil, et al., "Cell Contact but Not Junctional Communication (Dye Coupling) with Biliary Epithelial Cells is Required for Hepatocytes to Maintain Differentiated Functions," *Exper. Cell Res.*, 173 (1987) 524–533.

Michalopoulos, G., et al., "Primary Culture of Parenchymal Liver cells on Collagen Membranes," *Exper. Cell. Res.* 94 (1975) 70–78.

Millaruelo, Anal., "Role of Plasminogen Activator and its Inhibitors in Axonal Outgrowth and Regeneration In Vivo," *Caltech Biology*, (1987).

Mooney, David, et al., "Control of Hepatocyte Function Through Polymer–Substrate Modulation," Thesis Proposal–Department of Chemical Engineering, Massachusetts Institute of Technology (Sep. 22, 1989).

Movitz, David, "Accessory Spleens and Experimental Splenosis Principles of Growth," *The Chicago Medical School Quarterly*, vol. 26, No. 4, pp. 183–187 (Winter–Spring 1967).

Nastelin, Jennifer Green, "Pancreatic Islet Cell Transplantation: Optimization of Islet Cell Adhesion by Altering Polymer Surface Characteristics," Harvard–M.I.T. Division of Health Sciences and Technology (Feb. 1990).

Naughton, B. A., et al., "Granulopoiesis and Colony Stimulating Factor Production in Regenerating Liver," *Exp. Hematol.*, vol. 10, No. 5, pp. 451–458 (May 1982).

Naughton, B. A., et al., "Long–Term Growth of Rat Bone Marrow Cells in a Three–Dimensional Matrix," *The Anatomical Record*, vol. 18, No. 1, p. 97A (May 1987).

Naughton, G. K., et al., "Erythropoietin Production by Macrophages in the Regenerating Liver," *Journal of Surgical Oncology*, vol. 30, pp. 184–197 (1985).

Notter, M. F., et al., "Neuronal Properties of Monkey Adrenal Medulla In Vitro," *Cell Tissue Res.*, 244(1):69–76 (1986).

Nyilas E., et al., "Peripheral Nerve Repair with Bioresorbable Prosthesis," *Trans. Am. Soc. Artif. Intern. Organs*, 29:307–13 (1983).

Oellrich, R. G., et al., "Biliary Atresia," *Neonatal Network*, pp. 25–30 (Apr. 1987).

Omery, Anna, et al., "A Nursing Perspective of the Ethical Issues Surrounding Liver Transplantation," *Heart & Lung*, vol. 17, No. 6 (Nov. 1988).

Pasik, P., *Annals of the N.Y. Academy of Science*, vol. 495, pp. 674–675 (1987).

Patterson, P. H., et al., "Adrenal Chromaffin Cell–Derived Cholinergic Neurons for Brain Transplants," *Caltech Biology* (1987). p. 199.

Patterson, P. H., et al., *Caltech Biology*, (1987), pp. 201–202 #296.

Perlow, M. J., "Brain Grafting as a Treatment for Parkinson's Disease," *Neurosurgery*, vol. 20, No. 2, pp. 335–342 (1987).

Pimpl. et al., "Experimentelle Studie zur Frage der Transplntatkonditionierung and Transplantatgröfe Bei Heterotoper Autologer Milztransplantation," *Lagenbecks Archiv*, 37215–36218 (Salzburg 1984) Abstract only.

Pimpl. et al., "Perfusion of Autologous Splenic Grafts in Correlation with Specific Immunological Functions: An Experimental Study in Pigs," *Eur. Surg. Res.* vol. 19, 53–61 (1987).

Ptasinska–Urbanska, et al., "Intrascleral Introduction of Isolated Allogeneic Chondrocytes Capable of Cartilage Reformation in Rabbits; Possible Procedure in Treatment of Detachment of the Retina," *Exp. Eye Res.*, vol. 24, No. 3, pp. 241–247 (1977).

Redmond, D. E., Jr., et al., "Fetal Neuronal Grafts in Monkeys Given Methyphenyltetrahydropyridine," *The Lancet*, pp. 1125–1127 (May 17, 1986).

Redmond, D. E., Jr., et al., "Transplants of Primate Neurons," *Lancet*, 2(8514):1046 (Nov. 1, 1986).

Reid, L. M., et al., "Long–Term Cultures of Normal Ray Hepatocytes on Liver Biomatrix," *Ann. NY Acad. Sci.* (1980).

Rhine, et al., "Polymers for Sustained Macromolecule Release: Procedures to Fabricate Reproducible Delivery Systems and Control Release Kinetics," *Journal of Pharmaceutical Sciences*, vol. 69, No. 3 (Mar. 1980).

Rosen, Howard B., et al., "Bioerodible Polymers for Controlled Release Systems," *Controlled Release Systems: Fabrication Technology*, vol. II, Chapter 5, pp. 83–110 (1983).

Rosen, Howard B., et al., "Bioerodible Polyanhydrides for Controlled Drug Delivery," *Butterworth & Co.* (Publishers) Ltd. (1983).

Sapoznikova, et al., "Morphological Changes in Splenic Autografts Following Splenectomy: Experimental and Clinical Findings," *Biological Abstracts*, vol. 86, No. 76896 (1987), *Arkhiv Patologii*, vol. 49, No. 12, p. 37 (English Abstract–Moscow 1987).

Sasaki, K., "Neovascularization in the Splenic Autograft Transplanted into Rat Omentum as Studied by Scanning Electron Microscopy of Vascular Casts," *Virchows Arch. [Pathol. Anat.]*, vol. 409, 325–334 (1986).

Sawada, N., et al., "Effects of Extracellular Matrix Components of the Growth and Differentiation of Cultured Rat Hepatocytes," *In Vitro Cellular & Development Biology*, vol. 23, No. 4, pp. 267–273 (Apr. 1987).

Schmeck, Harold M., "Doctors Try to Capitalize on the Liver's Ability to Regenerate Itself," *The New York Times Medical Science* (May 16, 1989).

Seckel, B. R., et al., "Nerve Regeneration Through Synthetic Biodegradable Nerve Guides: Regulation by the Target Organ," *Plast Reconstr. Surg.*, 74(2):173–81 (Aug. 1974).

Shine, H. D., et al., "Cultured Peripheral Nervous System Cells Support Peripheral nerve Regeneration Through Tubes in the Absence of Distal Nerve Stump," *J. Neuroscience Res.*, 14(4):393–401 (1985).

Siegel, Ronald A., et al., "Controlled Release of Polypeptides and Other Macromolecules," *Pharmaceutical Research 1984*, pp. 2–10.

Sirica, Alphonse, et al., "Use of Primary Cultures of Adult Rat Hepatocytes on Collagen Gel–Nylon Mesh to Evaluate Carcinogen–Induced Unscheduled DNA Synthesis," *Cancer Research*, 40, 3259–3267 (Sep. 1980).

Sladek, J. R., Jr., et al., "Reversal of Parkinsonism by Fetal Nerve Cell Transplants in Primate Brain," *Annals of the New York Academy of Sciences*, vol. 495, pp. 641–657 (New York 1987).

Sladek, J. R., Jr., et al., "Survival and Growth of Fetal Catecholamine Neurons Transplanted into Primate Brain," *Brain Res. Bull.*, 17(6):809–18 (Dec. 1986).

Sladek, John R., Jr., et al., "Neural Transplantation: A Call for Patience Rather Than Patients," *Science*, vol. 240, pp. 386–388 (Jun. 10, 1988).

Sladek, John R., Jr., et al., "Transplantation of Fetal Dopamine Neurons in Primate Brain Reverses MPTP Induced Parkinsonism," *Progress in Brain Research*, vol. 71, pp. 309–323 (1987).

Stemple, Derek L., "A Factor that Induces Adrenergic Differentiation in Avian Neural Crest Cells," *Caltech Biology*, (1987).

Sudhakaran, P. R., et al., "Modulation of Protein Synthesis and Secretion by Substratum in Primary Cultures of Ray Hepatocytes," *Exper. Cell Res.* 167 (1986) 505–516.

Sullivan, Walter, "Spinal Injury Research Yields a Glimmer of Hope," *The New York Times*, (Jul. 14, 1987).

Tayassoli, Mehdi, et al., "Studies of Regeneration of Heterotopic Splenic Autotransplants," *Blood*, vol. 41, No. 5, pp. 701–709 (May 1973).

Thompson, John A., et al., "Heparin–Binding Growth Factor 1 Induces the Formation of Organoid Neovascular Structures In Vivo," *Proc. Natl. Acad. Sci. U.S.A.*, vol. 86, pp. 7928–7932 (Oct. 1989).

Thompson, J. A., et al., "Implantable Bioreactors: Modern Concepts of Gene Therapy," *Current Communications in Molecular Biology: Therapeutic Peptides and Proteins*, D. Marshak, ed., pp. 143–147 (Cold Spring Harbor Laboratory 1989).

Tomomura, Akito, et al., "The Control of DNA Synthesis in Primary Cultures of Hepatocytes From Adult and Young Rats: Interactions of Extracellular Matrix Components, Epidermal Growth Factor, and the Cell Cycle," *J. Cellular Physiology*, vol. 130, No. 1, pp. 221–227 (1987).

Unipoint Industries, Inc., "Polyvinyl Alcohol Foam for Surgical and Industrial Use" (May 1983).

UNOS Update, "National Cooperative Transplantation Study Completed," vol. 7, Issue 10 (Oct./Nov. 1991).

Vacanti, Joseph P., "Beyond Transplantation," *Arch. Surgery*, vol. 123, 545∝549 (May 1988).

Vargo, Rita, et al., "Infection as a Complication of Liver Transplant," *Critical Care Nurse*, vol. 9, No. 4, pp. 52–62 (1989).

Viig, J., et al., "UV–Induced DNA Excision Repair in Rat Fibroblasts During Immortalization and Terminal Differentiation in Vitro," *Exp. Cell Res.* 167 (1986) 517–530.

Yannas, I. V., et al., "Artificial Skin: A Fifth Route to Organ Repair and Replacement," *Iss. Polym. Biomaterial* 106, 221–230 (1986).

Yannas, I. V., et al., "Polymeric Template Facilitates Regeneration of Sciatic Nerve Across 15MM," *Polym. Material Sci. Eng.* 53, 216–218 (1985).

Masaaki Tachibana et al., *The Journal of Urology*, May 1985, vol. 133, No. 5 pp. 866–869.

Leeson et al. Histology 3rd W B Saunders Co. 1976 pp. 86, 87 & 114.

GENITOURINARY CELL-MATRIX STRUCTURE FOR IMPLANTATION INTO A HUMAN AND A METHOD OF MAKING

The United States Government has rights in this invention pursuant Grant No. 6M 26698 awarded by the National Institutes of Health.

REFERENCE TO RELATED APPLICATIONS

This application is continuation of U.S. Ser. No. 07/781,898, filed on Oct. 24, 1991, now abandoned, which is a continuation-in-part of U.S. Ser. No. 07/679,177, filed on Mar. 26, 1991, now abandoned, which is a continuation of U.S. Ser. No. 07/401,648, filed on Aug. 30, 1989, now abandoned, which is a continuation of Ser. No. 07/123,579, filed on Nov. 20, 1987, now abandoned, which is a continuation-in-part of U.S. Ser. No. 06/933,018, filed Nov. 20, 1986, now abandoned.

BACKGROUND OF THE INVENTION

The technical field of this invention is prosthetic surgery and cell culturing. In particular, the invention pertains to methods and implantable urological structures formed on biocompatible artificial matrices for the reconstruction or repair of urological structures.

Shortage of native urothelium places significant constraints on the success of surgical reconstruction in a wide variety of urologic conditions. Investigators have recognized this problem and have looked for alternatives for urothelial replacement. A variety of natural tissues, such as omentum and seromuscular grafts, and synthetic materials, such as polyvinyl sponge and Teflon, have been tried in experimental and clinical settings.

Unfortunately, these attempts have not produced satisfactory structural and functional replacement. Synthetic materials alone cannot replace selective transport functions of mucosal tissue and commonly are lithogenic in the urinary tract.

Bowel tissue has been used for urinary tract reconstruction for many years, however it is also associated with numerous complications. These include metabolic abnormalities, such as hyperchloremic metabolic acidosis arising from electrolyte reabsorption, infection, perforation, stone formation, increased mucous production, diverticular formation, and malignancy. Despite these problems, incorporation of intestinal segments into the urinary system has increased because of the lack of a suitable alternative.

A homologous substitute for urothelial tissues would be ideal. Recent work involving hypospadias reconstruction using bladder mucosal grafts demonstrates the potential of autologous replacement. See, for example, Hendren and Reda, Vol. 21 *J. Pediatric Surgery*, pp. 181–192 (1986) and Ransley et al., Vol. 58 *Brit. J. Urology*, pp.331–333 (1986). However, the limited availability of urothelial tissue for patients requiring major reconstruction involving the kidney, ureter, bladder or urethra generally precludes its use.

The use of reconstructed sheets of autologous urothelium in urinary tract reconstruction would be ideal for a variety of surgical procedures and would have the added advantage of avoiding immunologic rejection. Autologous skin keratinocytes have been used successfully in the treatment of extensive burn wounds. See, for example, Green et al., Vol. 76 *Proc. Nat'l. Acad. Sci.* pp. 5665–5668 (1979) and Burke et al., Vol. 194 *Ann, Surgery*, pp. 413–428 (1981). Keratinocytes derived from the urethral meatus have also been used in urethral grafts for hypospadias repair in humans as described in Romagnoli et al, Vol. 323 *New England J. Medicine*, pp. 527–530 (1990).

U.S. Ser. No. 679,177 entitled "Chimeric Neomorphogenesis Of Organs By Controlled Cellular Implantation Using Artificial Matrices" filed Mar. 26, 1991, and U.S. Ser. No. 933,018 entitled "Chimeric Neomorphogenesis Of Organs Using Artificial Matrices" filed Nov. 20, 1986, by Joseph P. Vacanti and Robert S. Langer, herein incorporated by reference, describe methods and means whereby cells having a desired function are grown on polymer scaffolding using cell culture techniques, followed by transfer of the cell polymer scaffold into a patient at a site appropriate for attachment, growth and function after attachment and equilibration to produce a functional organ equivalent. Success depends on the ability of the implanted cells to attach to the surrounding environment and to stimulate angiogenesis. Nutrients and growth factors are supplied during cell culture allowing for attachment, survival or growth as needed.

After the structure is implanted and growth and vascularization take place, the resulting organoid is a chimera formed of parenchymal elements of the donated tissue and vascular and matrix elements of the host. The polymer scaffolding used for the initial cell culture is constructed of a material which degrades over time and is, therefore, not present in the chimeric organ. Vascular ingrowth following implantation allows for normal feedback mechanisms controlling the soluble products of the implanted cells. The preferred material for forming the matrix or support structure is a biodegradable, artificial polymer, for example, polyglycolic acid, polyorthoester or polyanhydride, which is degraded by hydrolysis at a controlled rate and reabsorbed.

These materials provide the maximum control of degradability, manageability, size and configuration. In some embodiments, these materials are overlaid with a second material, such as gelatin or agarose, to enhance cell attachment. The polymer matrix must be configured to provide both adequate sites for attachment and adequate diffusion of nutrients from the cell culture to maintain cell viability and growth until the matrix is implanted and vascularization has occurred. The preferred structure for organ construction is a branched, fibrous, tree-like structure formed of polymer fibers having a high surface area which results in a relatively shallow concentration gradient of nutrients, wastes and gases so as to produce uniform cell growth and proliferation.

U.S. Ser. No. 933,018 and U.S. Ser. No. 679,177 disclose several examples of the successful culturing and implantation of hepatocytes, intestine, and pancreas cells, with subsequent normal function, including production and secretion of bioactive molecules. Examples of such molecules include growth hormone from pituitary cells, insulin and glycogen from pancreatic cells and clotting factors from liver cells. As described in these applications, however, there is a need for a different type of functioning "organ," one which provides primarily a structural function. Examples of types of cells which are useful in these applications include cartilage, bone and muscle cells.

It is an object of the present invention to provide a method and means for designing, constructing and utilizing artificial matrices as temporary scaffolding for cellular growth and implantation of urological structures.

It is a further object of the invention to provide biodegradable, non-toxic matrices which can be utilized for cell growth, both in vitro and in vivo, as supports for urological structures.

It is a still further object of the invention to provide biodegradable, non-toxic matrices which can be utilized for cell growth both in vitro and in vivo, to replace or to repair urological structures It is another object of this invention to provide an in vitro system in which cells will retain their normal morphology and cell function.

SUMMARY OF THE INVENTION

Methods and artificial matrices for the growth and implantation of urological structures and surfaces are disclosed.

In one aspect of the invention, urothelial cells are grown in culture on biodegradable, biocompatible, fibrous matrices formed of polymers, such as polyglycolic acid, polylactic acid, or other polymers which degrade over time, as a function of hydrolysis of the polymer backbone into innocous monomers. The matrices are designed to allow adequate nutrient and gas exchange to the cells until engraftment and vascularization at the site of engraftment occurs. The cells can be cultured in vitro until an adequate cell volume and density has developed for the cells to survive and proliferate in vivo, or maintained in vitro for the purpose of manufacturing bioactive molecules. Alternatively, when adequate cell numbers for implantation are available, the cells can be attached to the matrix and implanted directly, without proliferation in vitro. One advantage of the matrices is that they can be cast or molded such that the cells, when seeded on them, approximate the desired urological structure to be replaced or repaired, such as the urether, bladder, urethra, and the like. Implantation is followed by remodeling through cell growth and proliferation in vivo.

In another aspect of the invention, techniques are disclosed for establishing cultures of transitional uroepithelial cells which can be expanded in vitro using explant culture techniques, or in vivo using graft techniques. For example, as a first step in this approach, urothelial cells can be disassociated into single cell preparations, placed onto a synthetic substrate, and returned directly to animals or humans, where the normal reparative signals will direct regeneration, repair and remodelling. In addition, this approach allows the exploitation of the in vivo environment for the enhancement of growth in concert with the preservation of differentiated function.

In yet another aspect of the invention, techniques are disclosed for selectively extracting or harvesting urothelial cells either from excised urological tissue in vitro or from intact urological tissue in vivo by treating the tissue with a digestive enzyme, such as collagenase.

DETAILED DESCRIPTION

U.S. Ser. No. 679,177 entitled Chimeric Neomorphogenesis Of Organs By Controlled Cellular Implantation Using Artificial Matrices filed Mar. 26, 1991, by Joseph P. Vacanti and Robert S. Langer describes a technique of placing dispersed cell types onto synthetic, biodegradable polymer fibers in vitro which have been configured to produce high cell densities by allowing adequate diffusion of nutrients and waste as well as gas exchange. This technique has been applied to urothelial cells for the purpose of creating implants of urological structures, such as the urethers, bladder, urethra and the like.

In the preferred method, polymer fibers are placed in culture media containing urothelial cells, where the urothelial cells attach to the fibers in multiple layers and retain their normal configuration, which appears to be essential for the urothelial cells to maintain their normal function and remain viable. This technique also allows transplantation of the polymer cell scaffold into animals without disrupting the complex of attached urothelial cells. Transplantation of this complex containing a high density of normally-functioning urothelial cells with a large surface area into an animal allows the cells to obtain adequate nutrition by diffusion and successful engraftment of functioning urothelial tissue, even in the initial absence of vascularization.

The examples below demonstrate that it is possible to grow in culture on fibers of biodegradable polymers urothelial cells that appear to be morphologically and functionally normal and will proliferate to a cell density sufficient to allow implantation of the cell polymer scaffold in animals and successful engraftment with formation of a new tissue equivalent as the polymer resorbs. The examples also demonstrate that the polymer fiber scaffold is essential in that neither injection of free urothelial cells nor implantation of the polymer fibers without attached urothelial cells results in urological tissue formation.

The method and matrices providing structural and functional urological equivalents using bioabsorbable, artificial substrates as temporary scaffolding for cellular transfer and implantation reaffirms the principles first outlined in U.S. Ser. No. 933,018 filed Nov. 20, 1986:

1. Every structure in living organisms is in a dynamic state of equilibrium, undergoing constant renewal, remodeling and replacement of functional tissue which varies from organ to organ and structure to structure.
2. Dissociated structural cells tend to reform structure, depending on the environment in which they are placed and the degree of alteration which they have undergone.
3. Cell shape is determined by cytoskeletal components and attachment to matrix plays an important role in cell division and differentiated function. If dissociated cells are placed into mature tissue as a suspension without cell attachment, they may have difficulty finding attachment sites, achieving polarity and functioning because they begin without intrinsic organization. This limits the total number of implanted cells which can remain viable to organize, proliferate, and function.

The latter principle is a key point in the configuration of the urothelial cell support matrices. For an organ to be constructed in tissue culture and subsequently successfully implanted, the matrices must have sufficient surface area and exposure to nutrients such that cellular growth and differentiation can occur prior to the ingrowth of blood vessels following implantation. After implantation, the configuration must allow for diffusion of nutrients and waste products and for continued blood vessel ingrowth as cell proliferation occurs.

Urothelial cells are initially isolated and cultured using a novel technique. Digestive enzymes such as collagenase, trypsin or EDTA can be used to isolate urothelial cells for recovery and seeding purposes. In one approach, a urothelial biopsy sample can be taken and the mucosa stripped away and placed in an enzyme solution, such as an aqueous collagenase solution having an enzyme concentration from about 0.1 to about 0.75 percent. The urothelial cells will be liberated and can then be collected by centrifuging or the like. Alternatively, a catheter can be introduced into the bladder to fill the bladder with an enzyme solution (e.g., a milder collagenase solution from about 0.05 to about 0.40 percent collagenase). Following irrigation of the bladder and collection of the rinses, urethelial cells can again be collected and used to seed a polymeric matrix.

Once the cells have begun to grow and cover the matrix, they are implanted in a patient at a site appropriate for attachment, growth and function. One of the advantages of a biodegradable polymeric matrix is that angiogenic and other bioactive compounds can be incorporated directly into the matrix so that they are slowly released as the matrix degrades in vivo. As the cell polymer structure is vascularized and the structure degrades, the cells will differentiate according to their inherent characteristics.

In the preferred embodiment, the matrix is formed of a bioabsorbable or biodegradable, synthetic polymer, such as a polyanhydride, polyorthoester or polyglycolic acid. In some embodiments, attachment of the cells to the polymer is enhanced by coating the polymers with compounds, such as basement membrane components, agar, agarose, gelatin, gum arabic, collagens, fibronectin, laminin, glycosaminoglycans, mixtures thereof, and other materials having properties similar to biological matrix molecules known to those skilled in the art of cell culture. All polymers must meet the mechanical and biochemical parameters necessary to provide adequate support for the cells with subsequent growth and proliferation. Factors, including nutrients, growth factors, inducers of differentiation or dedifferentiation, products of secretion, immunomodulators, inhibitors of inflammation, regression factors, biologically-active compounds which enhance or allow ingrowth of the lymphatic network or nerve fibers, and drugs, can be incorporated into the matrix or provided in conjunction with the matrix. Similarly, polymers containing peptides, such as the attachment peptide RGD (Arg-Gly-Asp) can be synthesized for use in forming matrices.

A presently-preferred polymer is Polyglactin, developed as absorbable synthetic suture material, a 90:10, copolymer of glycolide and lactide, manufactured as VICRYL™ braided absorbable suture (Ethicon Co., Somerville, N.J.) See, Craig et al.: A Biological Comparison Of Polyglactin 910 And Polyglycolic Acid Synthetic Absorbable Sutures. Vol. 141, *Surg.*, p. 1010 (1975). Polyglycolide fibers can be used as supplied by the manufacturer. Other shapes can be fabricated using one of the following methods:

Solvent Casting. A solution of polymer in an appropriate solvent, such as methylene chloride, is cast as a branching pattern relief structure. After solvent evaporation, a thin film is obtained.

Compression Molding. Polymer is pressed (30,000 psi) into an appropriate pattern.

Filament Drawing. Filaments are drawn from the molten polymer.

Meshing. A mesh is formed by compressing fibers into a felt-like material.

The polymers can be characterized with respect to mechanical properties, such as tensile strength using an Instron tester, for polymer molecular weight by gel permeation chromatography (GPC), glass, transition temperature by differential scanning calorimetry (DSC) and bond structure by infrared (IR) spectroscopy; with respect to toxicology by initial screening tests involving Ames assays and in vitro teratogenicity assays and implantation studies in animals for immunogenicity, inflammation, release and degradation studies. In vitro cell attachment and viability can be assessed using scanning electron microscopy, histology and quantitative assessment with radioisotopes.

At the present time, a mesh-like structure formed of fibers, which may be round, scalloped, flattened, star shaped, solitary or entwined with other fibers is preferred. The use of branching fibers is based upon the same principles which nature has used to solve the problem of increasing surface area proportionate to volume increases. All multicellular organisms utilize this repeating branching structure. Branching systems represent communication networks between organs, as well as the functional units of individual organs. Seeding and implanting this configuration with cells allows implantation of large numbers of cells, each of which is exposed to the environment of the host, providing for free exchange of nutrients and waste while neovascularization is achieved.

The polymeric matrix may be made flexible or rigid, depending on the desired final form, structure and function. For reconstruction of kidney structures such as the renal pelvis as well as for reconstruction of bladder, sheet-like matrices may be preferable in many instances. For reconstruction of the urethra and/or ureters, tubular matrices will often be preferable.

Cells may be derived from the host, a related donor or from established cell lines. In one variation of the method using a single matrix for attachment of one or more cell lines, the scaffolding is constructed, such that initial cell attachment and growth occur separately within the matrix for each population, for example, urothelial and non-urothelial cell populations. Alternatively, a unitary scaffolding may be formed of different materials to optimize attachment of various types of cells at specific locations. Attachment is a function of both the type of cell and matrix composition.

The following non-limiting examples demonstrate actual attachment of cell preparations to bioerodible, artificial polymers in cell culture and implantation and engraftment of this polymer-cell scaffold into animals. These examples describe methods of harvesting primary uroepithelial cells from rabbits and demonstrate the use of biodegradable polyglycolic acid polymer matrices as vehicles for delivery and maintenance of urothelium in host animals to create new urothelial tissue in vitro.

EXAMPLES

Young adult New Zealand white rabbits (Charles River Labs, Wilmington, Mass.) were used as cell donors for all experiments. Young adult athymic nu/nu mice (Charles River Labs) were used as cell recipients. The animals were housed individually, allowed access to food and water ad lib, and maintained at 12 hr light and dark intervals. Anesthesia for rabbits was carried out with an intramuscular injection of ketamine and rompum. Mice were anesthetized with Enfluorane by cone administration.

Biodegradable polymers were obtained as nonwoven meshes of polyglycolic acid, a synthetic polymer of hydroxyacetic acid (Davis and Geck, Danbury, Conn.). The average fiber diameter was 15 Mm. Interfiber distances varied between 0 and 200 Mm. Dimensions of the polymer meshes used for implantation were 0.75×0.75 cm. Polymers were sterilized in ethylene oxide and sealed in aluminum foil until implantation.

Rabbit urothelial cells (RUC) for transplantation were isolated using the following method of cell harvesting. After the induction of anesthesia, the shaved abdomens of rabbits were painted with betadine and opened using sterile technique. The bladders were isolated, the ureters ligated and the urethras cannulated. The bladders were rinsed with 3–5 ml of sterile phosphate buffered saline (PBS) and filled with a buffered collagenase solution comprised of 0.1–0.75% collagenase B from Cl. histolyticum (Boehringer Mannheim, Indianapolis, Ind.) and sealed.

The ligated bladders were then placed in a 50 ml conical tube with the remaining volume filled with PBS and incubated in a water bath at 37° C. Incubation time was varied. Urothelial cell suspensions were recovered from the donor bladders, washed with a 4:1 mixture of DMEM and Ham's F12 medium (Gibco, Grant Island, N.Y.) supplemented with 25 mg/ml adeninine, 0.244 mg/ml biotin, 0.0136 ng/ml triiodothyronine, 5 mg/ml insulin, 5 mg/ml transferrin, and penicillin and strepotomycin, and pelleted in a clinical centrifuge. Cell resuspension and centrifugation was carried out an additional two times.

The cells were then counted with a hemacytometer and their viability determined by the Trypan Blue exclusion method. The urothelial cells were then seeded onto polyglycolic acid biodegradable polymers and were maintained at 37° C. in a humidified atmosphere of 95% air/5% $CO_2$. After 1 to 4 days in culture, the polymers were implanted into the retroperitoneum, subcutaneous tissue or omentum of athymic mice. Implants were then retrieved at sacrifice at 5, 10, 20 and 30 days. Polymers implanted without cells served as controls. Implants were examined histologically and by western blot.

Implants recovered from host animals were fixed in 10% neutral buffered formalin and embedded in paraffin. Paraffin sections were stained with hematoxylin and eosin.

Protein fractions enriched in cytoskeletal proteins, according to protein isolation protocol described in Freeman and Sueoka, Vol. 84, *PNAS*, pp. 5808–5812 (1987), were separated on 10% polyacrylamide gels according to the procedure of Laemmli. Approximately 15 mg protein was loaded per lane. Proteins were electrophoretically blotted onto Immunobilon-P blotting membranes (Millipore, Bedford, Mass.). Non-specific sites were blocked in: 1% (w/v) Carnation non-fat dry milk, 0.5% (v/v) Tween 20, 150 mM NaCl, 20 mM Tris base. AE1 and AE3 monoclonal antibody mixture (Boehringer Mannheim) was incubated at 2 mg/ml in blocking buffer for 2 hr at room temperature.

After repeated washes with blocking buffer, the membrane was incubated for 2 hr with anti-mouse IgG linked to alkaline phosphatase (Bio-Rad, Richmond, Calif.) at 1:3000 dilution. Membranes were washed repeatedly in blocking buffer, then in substrate buffer (100M Tris base, 100 mM NaCl, 50 mM $MgCl_2$, pH9.5) Colorimetric detection was with the NBT/BCIP color reagent (Bio-Rad) until the bands were adequately visualized.

The objective of these experiments was to determine whether newly harvested urothelial cells would attach to biodegradable polymers in vitro and whether these polymers would serve as a suitable synthetic substrate for delivery and maintenance of epithelial architecture in vivo. Explant techniques have generally been used for the establishment of primary cultures of uroepithelial cells. However, for the experiments described here, the use of explant cultures would not provide an adequate number of cells. Therefore, a method was developed that would allow isolation of bladder cell populations efficiently, and in which large quantities of cells enriched in uroepithelia can be obtained rapidly and quantitatively. One approach was to excise freshly-irrigated bladders from rodents and to treat the mucosal surface with collagenase by incubating the proteolytic enzyme solution within the enclosed, ligated bladder for various times.

Initial attempts at cell harvest with this method using Fisher rats resulted in the recovery of less than $5\times10^4$ viable cells per bladder and, although a limited sequence of implants into syngeneric hosts was carried out using these cells, this approach was later abandoned. In subsequent trials, in which bladders were obtained from New Zealand white rabbits, adequate numbers of cells were obtained reproducibly. Attempts to optimize the cell harvest method by varying incubation time and collagenase concentration resulted in establishment of one preferred condition of incubation for 2 hr at 37° C. in 0.5% collagenase. Assessment of cell viability using the Trypan Blue exclusion method indicated that these conditions resulted consistently in the recovery of the greatest number of viable cells. Quantitation of cell recovery by cell counting over an extended period indicated that this method resulted in an average recovery of $1.7\times10^6 \pm 1.01\times10^5$ viable cells/bladder (n=32).

Morphological analysis of these cell populations plated onto plastic surfaces by phase contrast microscopy indicated that they were composed largely of uroepithelial cells, with very little fibroblast contamination evident within the first five days in culture. With maintenance of the cultures for later times, fibroblast outgrowth occurred. This result suggests that this method of cell harvest results in recovery of populations enriched in urothelium and that these populations can be maintained as relatively homogeneous cultures at least for several days.

Rabbit uroepithelial cells (RUC) obtained using this cell harvest method were seeded directly onto nonwoven polyglycolic polymers of approximately 0.56 $cm^2$ surface area in culture and allowed to attach from between 1 to 4 days. Cell attachment to the polymers occurred readily as assessed by phase contrast microscopy with only limited numbers of floating cells, indicating that under our conditions, cultures enriched in healthy, viable cells were obtained routinely. In most experiments polymer-cell allografts were implanted into host animals after incubation in culture medium overnight.

Allografts containing RUC were surgically implanted in the mesentery, retroperitoneum, or subcutaneous tissue of athymic (nude) mice (not greater than three implants per animal) and recovered at varying times after implantation. Twenty-eight adult New Zealand white rabbits were used as donors for cell harvest. Thirty-three nude mice were used as recipients. Not including host animals lost by attrition, a total of 58 cell-polymer scaffolds were recovered from host animals at 5 to 30 day time points. A total of 17 polymers implanted without cells and maintained in vivo for the respective times served as controls.

Histologic analysis demonstrated an inflammatory response, which exhibited both an acute phase and a chronic foreign body reaction. Fibroblast infiltration and proliferation were seen up to 10 days after implantation. Vascular ingrowth was apparent in most implants by 5 days. Control polymers elicited similar inflammatory and angiogenic responses, suggesting that these responses were largely due to the polymers.

Epithelial cells were evident in a substantial fraction of RUC-polymer implants recovered at each time point, including the allografts maintained in vivo for 30 days. Epithelial layers were frequently found associated with polymer fibers. The number of implants containing identifiable urothelial cells was highest at the 5 day time point (89%). Single cell layers were evident in 10 day implants and multiple epithelial cell layers were evident in 20 day and 30 day implants. Recognizable epithelial populations were not evident in any of the 17 control polymers.

These results indicate that RUC can survive and can remain associated with the polymer fibers at the ectopic implant sites even after extended periods in vivo.

Western blot analysis of protein fractures obtained from 30 day RUC-polymer implants demonstrated the presence of a prominently-expressed 40 kDa cytokeratin present in rabbit bladder uroepithelium, identified using the AE1 and AE3 anticytokeratin monoclonal antibodies. In this assay, this cytokeratin expression pattern can be distinguished from that seen using protein from mouse skin. Cytokeratins were not identifiable in protein fractions from control polymers implanted without cells. This result suggests the potential for maintenance of uroepithelial differentiation in implants maintained in host animals for long periods at ectopic sites. This result also confirms the histologic assessment that eosinophilic cell types present in the polymer allografts at late time points are RUC.

In summary, the feasibility of using biodegradable polymers as delivery vehicles for urothelial cell populations in vivo has been demonstrated. Primary rabbit urothelial cells (RUC) were found to attach readily to unwoven polyglycolic acid polymers in vitro. Polymer-RUC allografts were found to contain viable RUC after implantation times for as long as 30 days at ectopic sites in athymic mice, although some RUC cell death in the implants was noted. Polymers were seen to evoke an angiogenic response, which should allow RUC populations to survive, and possibly proliferate, after extended periods in vivo. RUC oriented themselves spatially along the polymer surfaces and RUC populations appeared to expand from one to several cell layers in thickness with extended times of implantation.

Western blot analysis confirmed the presence of a cytokeratin protein associated with rabbit bladder urothelium in implants recovered after 30 days. This results suggests that some cell type-specific functions associated with bladder differentiation may be retained in implants after extended periods. We have also presented an efficient method of uroepithelial cell harvest which will allow the efficacy of reconstitution of urothelial cell growth, structure and function to be studied more extensively in this model system.

Reconstructive procedures involving the bladder, ureters, urethra and kidney frequently employ bowel segments, despite the potential for numerous complications. The benefit of using bladder mucosa in these procedures is self-evident, however a suitable urothelial substitute for bowel would require the creation of autologous urothelial sheets, most likely originating from limited biopsy material. Harvesting and expansion of autologous urothelium, in the manner successfully employed with skin, may not be possible, due to the relatively limited proliferative potential of differentiated uroepithelium in vitro. This limitation may be overcome by use of molecular regulators of uroepithelial growth and differentiation.

The present study provides evidence that the creation of urothelial structures de novo from diassociated urothelial cells can be achieved in vivo using biodegradable polymers as delivery vehicles. Unwoven polyglycolic acid polymers provided an adequate surface for urothelial cell attachment and were found to serve as suitable substrates for urothelial survival, and possibly growth, in vivo. Further, RUC on these polymers were found to orient themselves spatially in the host animals, and to exhibit some aspects of urothelial cell differentiation (cytokeratin expression), even after extended periods. Significantly, contiguous layers of presumptive uroepithelium were identified in most of the RUC-polymer implants found to contain eosinophilic cells, even though the cell harvest procedure involved the isolation and seeding of suspensions of single cells. This indicates that these polymers can support the spontaneous reorientation of uroepithelium into layered structures resembling normal transitional cell architecture.

Some differentiated cell types, such as chondrocytes and hepatocytes, have been found to remain functionally differentiated and in some cases to expand in vivo on nonwoven polyglycolic acid or polylactic acid polymers. The polymer fibers provide sites for cell attachment, the reticular nature of the polymer lattice allows for gas exchange to occur over considerably less than limiting distances, and the polymers evoke host cell responses, such as angiogenesis which promote cell growth.

Synthetic polymers can also be modified in vitro before use, and can carry growth factors and other physiologic agents such as peptide and steroid hormones, which promote proliferation and differentiation. The malleability of the synthetic polymer used in this study also should allow for the creation of cell-polymer implants manipulated into preformed configurations (e.g., tubes in the case of urothelium).

In genitourinary reconstruction, cell-polymer allografts can be implanted along existing urinary structures in manipulated forms resembling normal in vivo architecture. The polyglycolic acid polymer undergoes biodegradation over a four month period; therefore as a cell delivery vehicle it permits the gross form of the tissue structure to be reconstituted in vitro before implantation with subsequent replacement of the polymer by an expanding population of engrafted cells.

The newly-developed urinary structure can thereby mimic the gross configuration of the polymer scaffold, be composed of transplanted uroepithelial cells and their derivatives, be functional in situ, and possibly be translatable to another site in a reconstructive procedure.

Although this invention has been described with reference to specific embodiments, variations and modifications of the method and means for constructing urothelial implants by culturing urothelial cells on matrices having maximized surface area and exposure to the surrounding nutrient-containing environment will be apparent to those skilled in the art. Such modifications and variations are intended to come within the scope of the appended claims.

We claim:

1. A genitourinary cell-matrix structure for implantation into a human comprising:

a biocompatible, biodegradable polymeric matrix comprising a plurality of fibers in a nutrient environment; and parenchymal cells of human genitourinary origin attached to and within the matrix in vitro, wherein the matrix provides a scaffold for cell attachment and has a surface area sufficient to provide free exchange of nutrients and waste by diffusion for attached cells to survive in vitro prior to implantation and in the absence of vascularization, and wherein the matrix is formed in a shape for reconstruction of a genitourinary structure.

2. The structure of claim 1 wherein the polymer is selected from the group consisting of polyanhydride, polyorthoester, polyglycolic acid, polylactic acid and combinations thereof.

3. The structure of claim 1 further comprising coatings on the the polymer selected from the group consisting of basement membrane components, agar, agarose, gelatin, gum arabic, collagens, fibronectin, laminin, glycosaminoglycans, attachment peptides, and mixtures thereof.

4. The structure of claim 1 wherein the matrix forms a flexible structure conformable to a biological surface.

5. The structure of claim 1 wherein the matrix is formed of a mesh of open nonwoven fibers.

6. A method for making a genitourinary cell-matrix structure for implantation into a human comprising:

providing a biocompatible, biodegradable polymeric matrix comprising a plurality of fibers in a nutrient environment; and allowing parenchymal cells of human genitourinary origin to attach to and within the matrix to form a genitourinary structure in vitro, wherein the matrix provides a scaffold for cell attachment and has a surface area sufficient to provide free exchange of nutrients and waste by diffusion for the attached cells to survive in vitro prior to implantation and in the absence of vascularization.

7. The method of claim 6 wherein the polymer is selected from the group consisting of polyanhydride, polyorthoester, polyglycolic acid, polylactic acid and combinations thereof.

8. The method of claim 6 further comprising coating the polymer with a material selected from the group consisting of basement membrane components, agar, agarose, gelatin, gum arabic, collagens, fibronectin, laminin, glycosaminoglycans, attachment peptides, and mixtures thereof.

9. The method of claim 6 wherein the matrix is formed as a flexible structure conformable to a biological surface.

10. The method of claim 6 further comprising implanting the structure to form a urological prosthesis.

11. The method of claim 6 further comprising allowing the cells to attach on a matrix, allowing the cells to proliferate on the matrix in vitro in a nutrient media, then implanting the matrix in vivo.

* * * * *

UNITED STATES PATENT AND TRADEMARK OFFICE
CERTIFICATE OF CORRECTION

PATENT NO.  : 5,567,612
DATED       : October 22, 1996
INVENTOR(S) : Joseph P. Vacanti
              Robert S. Langer It is certified that error appears in the above-indentified patent and that said Letters Patent is hereby corrected as shown below:

On the title page, item [75] should read ---Joseph P. Vacanti and Robert S. Langer--.

Signed and Sealed this

Twenty-third Day of September, 1997

BRUCE LEHMAN

*Attest:*

*Attesting Officer*  *Commissioner of Patents and Trademarks*